United States Patent [19]

Mallis

[11] 3,960,759
[45] June 1, 1976

[54] LIQUID VESICANT DIFFERENTIATING PAINT

[75] Inventor: James N. Mallis, Fredericksburg, Va.

[73] Assignee: The United States of America as represented by the Secretary of the Navy, Washington, D.C.

[22] Filed: Nov. 24, 1965

[21] Appl. No.: 510,166

[52] U.S. Cl. .............................. 252/408; 106/290; 106/300; 106/304; 106/306
[51] Int. Cl.² .......................................... C09K 3/00
[58] Field of Search ............ 252/408; 106/287, 300, 106/316, 290, 304, 306

[56] References Cited
UNITED STATES PATENTS

| | | | |
|---|---|---|---|
| 2,926,072 | 2/1960 | Kramer | 252/408 X |
| 3,087,794 | 4/1963 | Free et al. | 252/408 X |

*Primary Examiner*—Stephen J. Lechert, Jr.

[57] ABSTRACT

There is described an indicator paint for use in painting the exterior surface of rockets, etc., designed to carry H, G and V agents. The paint is composed of two dyestuffs mixed with a vinyl-acrylic copolymer latex, plus various other chemicals which will react by changing to a certain color upon contact by one of the above cited agents.

4 Claims, No Drawings

LIQUID VESICANT DIFFERENTIATING PAINT

The invention described herein may be manufactured and used by or for the Government of the United States of America for governmental purposes without the payment of any royalties thereon or therefor.

This invention relates to a detector paint light in color to be used on various vehicles designed to carry toxic chemical warfare agents of the respective classes commonly known as H, G and V agents; H is the accepted symbol for mustard gas, while G and V are the accepted symbols for two basic types of nerve gases. More particularly, the present invention relates to a light colored coating used to function as a detector for the presence of toxic agents by indicating agent contaminated surfaces and by differentiating among various agents.

Presently, detector paints for toxic chemical agents fail to meet current military color requirements for the coating of various military hardware, and fail to readily disclose the presence of agent spills, leaks and contamination because they are dark in color. The ability of these paints to withstand elevated temperatures has been found to be inferior and their storage life is usually of short duration. Also, these paints fail to possess those properties which permit them to act both as detecting means and as means clearly distinguishing between the different toxicants upon detection.

Accordingly, it is an object of the invention to provide a composition which is white or slightly colored, for the detection of toxic chemical agents which can be employed in the form of a liquid vesicant paint.

Another object is to provide a light paint which indicates the presence of chemical toxic agents and is capable of vividly differentiating one of such agents from another.

Another object is to provide a white or lightly colored detector which is easy to formulate into a finished coating, can be mass produced and is economical in large quantity use.

Another object is to provide a latex base coating which will react in the presence of a specific toxic agent to form a distinctive coloration.

Another object is to provide a white or slightly colored coating containing two dyestuffs which coating reacts upon contact by various toxic agents in a different manner for different toxicants.

Other objects, advantages and novel features of the invention will become apparent from the following detailed description of the invention with the understanding that the ingredients used may be varied without departing from the invention.

The liquid vesicant differentiating paint of the instant invention contains two dyestuffs that are mixed with a vinyl-acrylic-copolymer latex at concentrations of approximately ½ to 1½% each by weight, along with celite, titanium dioxide and water to complete the formulation. The dyestuff materials are: 2, 5, 2', 5' -tetramethyl triphenylmethane-4, 4'-diazo-bis-B-hydroxynaphthoic anilide; and ethyl-bis-(2, 4-dinitrophenyl)-acetate. The titanium is used to contribute to the whiteness of the paint.

The coating, being white or only slightly colored clearly reveals the presence of agent spills, leaks and contamination upon reaction by displaying a particular color which is a definitely observable reaction distinct to at least one or more of the different ones of the agents. Exposure to extreme weather temperatures of −65° F and 140° F results in no change in the original coating after an interval of 30 days. It becomes dry to the touch in one-half hour and responds rapidly (less than 3 seconds) to agent simulants. It possesses and excellent shelf life and can be easily applied to primed metal surfaces or any type surface thereby functioning as an exterior type latex base coating with the typical outdoor weathering resistance found in commercial types. The specific dyestuffs involved act to discolor the latex base coating to a very small degree or not at all since they possess those latent qualities which stain the paint only upon exposure to a specific toxicant. The dyestuffs do not dissolve the latex base paint nor do they affect it's efficiency. This coating exhibits definitely discernable color changes of violet, red and blue upon contact with minute quantities of the G, H and V agent simulants respectively. It reacts to caustic materials by changing to a pale green but it does not react with alcohols. The green color obtained by contact with caustic is, however, not due to the dyes present in the paint. It is due to the attack of caustic upon the zinc chromate primer used on metal surfaces. The paint formulation permits this reaction.

The dyestuffs, if finely divided, may be incorporated in a styrene-butadiene base or acrylic base latex paint directly to produce a working formulation. However, its stability to high temperatures and sunlight and its rapid response to the toxic agents is sacrificed somewhat when these latexes are used.

Other possible uses of the detection paint may be various shipboard surfaces where vesicant detection capabilities are deemed desireable, plane fuselages, decontamination equipment, shipdecks, etc. It can function as a camouflage coating during tactical use, as an indicator of leaks during storage and as a detector in areas under chemical warfare attack.

Obviously, any modifications and variations of the present invention are possible in light of the above teachings. It is therefore to be understood that within the scope of the appended claims the invention may be practiced otherwise than as specifically described.

What is claimed is:

1. A liquid vesicant paint, light in color, for use in detecting the presence of toxic agents, selected from the group consisting of mustard and nerve gases, in the air or on vehicle surfaces, which paint when in use reacts to the presence of said agents by displaying a particular color which is a definitely observable reaction distinct to at least one or more of the different ones of said agents, said paint containing essentially:

a mixture of a latex base, two dyestuffs present in formulation at concentration of approximately 1% each, by weight, celite, titanium dioxide and water, wherein;

said dyestuff materials are 2, 5, 2', 5'-tetramethyl triphenylmethane-4, 4'-diazo-bis-B-hydroxynaphthoic anilide; and, ethyl-bis-(2, 4-dinitrophenyl)-acetate.

2. The paint of claim 1 wherein said latex base is a vinyl-acrylic copolymer latex.

3. The paint of claim 1 wherein said latex base is styrene-butadiene latex.

4. The paint of claim 1 wherein said latex base is an acrylic latex.

* * * * *